United States Patent [19]

Campbell et al.

[11] 4,206,180

[45] Jun. 3, 1980

[54] OXYCHLORINATION OF ETHYLENE

[75] Inventors: Ramsey G. Campbell, Berkeley; Elliott P. Doane, Moraga; M. Henry Heines, Oakland; Joseph S. Naworski, Martinez; Harvey J. Vogt, Lafayette, all of Calif.

[73] Assignee: Stauffer Chemical Company, Westport, Conn.

[21] Appl. No.: 948,943

[22] Filed: Oct. 6, 1978

Related U.S. Application Data

[60] Division of Ser. No. 686,333, May 14, 1976, Pat. No. 4,123,467, which is a continuation-in-part of Ser. No. 595,465, Jul. 14, 1975, abandoned.

[51] Int. Cl.$^2$ .................... B01J 8/04; C07C 17/10; C07C 17/08
[52] U.S. Cl. .................... 422/190; 260/654 A; 260/658 R; 260/659 A; 260/662 A
[58] Field of Search .......... 260/659 A, 654 A, 658 R, 260/662 A; 422/190

[56] References Cited

U.S. PATENT DOCUMENTS

| | | | |
|---|---|---|---|
| 3,184,515 | 5/1965 | Penner et al. | 260/658 R |
| 3,699,178 | 10/1972 | Suzuki et al. | 260/659 A |
| 3,892,816 | 7/1975 | Kister | 260/659 A |

FOREIGN PATENT DOCUMENTS

| | | | |
|---|---|---|---|
| 820547 | 4/1975 | Belgium | 260/659 A |
| 517009 | 9/1955 | Canada | 260/659 A |
| 1104666 | 2/1968 | United Kingdom | 260/659 A |

Primary Examiner—Barry S. Richman
Attorney, Agent, or Firm—Joel G. Ackerman

[57] ABSTRACT

Oxychlorination of ethylene is carried out using a three-reactor system containing beds of a catalyst comprising a spherical, high-surface area activated alumina impregnated with cupric chloride and potassium chloride. In the first two reactors, the catalyst bed is divided into two sections, with a more active catalyst in the lower section than in the upper. The catalyst is substantially undiluted with inert particles.

A new catalyst for such a process is also provided.

21 Claims, 1 Drawing Figure

OXYCHLORINATION OF ETHYLENE

CROSS-REFERENCE TO RELATED APPLICATIONS

This is a division of our application Ser. No. 686,333, filed May 14, 1976, and now U.S. Pat. No. 4,123,467 issued Oct. 31, 1978, which is in turn a continuation-in-part of application Ser. No. 595,465, filed July 14, 1975 and now abandoned.

BACKGROUND AND PRIOR ART

This invention relates to the oxychlorination of ethylene in a fixed bed catalytic process to produce chlorinated hydrocarbons, particularly 1,2-dichloroethane.

It is well known that hydrocarbons such as ethylene may be chlorinated by reacting them with hydrogen chloride and gases containing elemental oxygen, particularly air, in the presence of a catalyst at elevated temperatures and pressures. Such a process is generally termed on "oxychlorination" or a Deacon process and usually employs a catalyst comprising a chloride of a metal having at least two valences, generally on a porous refractory support. The most common catalyst for such processes comprises cupric chloride on a particulate material such as activated alumina, silica, alumina-silica, diatomaceous earth, etc. Activated alumina, in one or another of its various forms, is the most common support utilized. In addition, the catalyst may contain additives such as alkali metal chlorides, rare earth metal chlorides, and other metallic compounds which assist in promoting the desired reaction and/or inhibiting the progress of side reactions. Particularly, potassium chloride has been utilized as an additive to such a catalyst when it is desired to produce 1,2-dichloroethane from ethylene since potassium chloride is known to suppress the formation of ethyl chloride. The amount of potassium chloride used, however, is kept low as it also tends to decrease the activity of the catalyst towards the primary reaction.

In the conduct of such a fixed bed oxychlorination process one of the concerns is the control of the reaction temperature. The oxychlorination reaction itself is highly exothermic and, in addition, control of the reaction temperature is hampered by the fact that the catalyst bed itself has a low heat conductivity. As a result of these two factors, there is a danger of the formation of undesirably extraordinarily high localized temperature zones in the catalyst bed. Numerous expedients have been proposed in the art aimed at preventing or at least minimizing the existence of such exceptionally high localized temperatures. For example, it has been variously proposed to control temperature by adjusting the ratio of the reactants; by diluting the feed with an inert gas or an excess of one or more reactant gases; by utilizing a tubular reactor with controlled external cooling and/or tubes of varying diameters; by diluting the catalyst particles with inert particles; and by varying the particle size of the catalyst and/or inert particles.

Particularly when the reaction is conducted in tubular reactors, it is known in the art, for example as described in U.S. Pat. No. 3,184,515, that the problem of undesirably high localized temperatures does not exist throughout the entire reactor. This is a result of the nature of the oxychlorination reaction itself, which becomes progressively less vigorous in the direction of flow of the reaction mixture. At the inlet of the catalyst bed, the reaction proceeds rapidly and strongly and control of both the temperature and location of the hot spot (point of highest temperature) in the bed is important. However, as the reactants proceed through the bed, the reaction becomes somewhat less vigorous as oxygen is consumed. This is particularly the case when, as is known in the art, the oxychlorination process is carried out in a series of two or more catalytic reactors with the total air (or oxygen) feed being split between the several reactors. Thus, as the oxychlorination feed mixture reacts, oxygen is used up toward the outlet of each reactor and the concern of a runaway reaction or overly high localized temperature in this zone is less than in the portion of the reactor closer to the inlet.

One solution which has been proposed for accomplishing acceptable conversions and selectivity to dichloroethane as well as obtaining reasonable control of the reaction temperatures and formation of high localized temperatures is to dilute the catalyst with inert particles intermingled with the catalyst particles. The inert particles may consist of, for example, silica, alumina, graphite, glass beads, etc. In some processes, the proportions of catalyst to diluent in the oxychlorination reactor have been varied. At the inlet side of the reactor, it is desirable to have a less concentrated catalyst because of the danger of runaway reactions or high localized temperatures. However, further from the inlet, as the reaction proceeds and becomes less vigorous, these dangers are not quite so prominent and in fact, it would be desirable to have a more highly active catalyst to continue promoting the reaction as oxygen is consumed. Thus, it is common when using diluted catalysts to divide the bed into two or more zones, each zone containing a different ratio of catalyst to diluent, with the ratio of catalyst to diluent increasing toward the outlet end of the reactor. For example, in U.S. Pat. No. 3,184,515, a process is described (Example 1) using a diluted catalyst in which the reaction tube is divided into four zones, the first zone containing 7 volume percent catalyst and 93 volume percent graphite diluent, the second zone containing catalyst to diluent in a 15:85 volume percent ratio, the third containing a 40:60 mixture, and the fourth containing 100 percent catalyst. In another variation, a fairly highly active catalyst may be placed at the very inlet of the reactor in order to initiate the reaction, immediately followed by a much less active catalyst to prevent the formation of hot spots in the adjacent reaction zone.

The use of a diluted catalyst such as described in the preceding paragraphs, however, possesses several disadvantages. In the first place, it requires loading of the catalyst in several different reaction zones and thus, the formulation of several catalyst-diluent mixtures of different proportions. Of greater concern however, is the fact that the mixing of catalyst and diluent can result in a non-uniform mixture. There is, therefore, a likelihood of formation of undesirably high localized temperatures due to a concentration of catalyst particles in a particular section of the reaction zone if the mixing is not carried out to a sufficiently thorough degree. Additionally, in many cases the diluent particles are not of the same general size or shape as the catalyst particles. It has been proposed, for instance, to dilute cylindrical catalyst particles or spherical catalyst particles with diluent particles of a different shape or size. In such cases, the overall mixture does not provide a reasonably uniform surface to the reactants and the pressure and/or pressure drops occurring during the reaction may be other than advantageous. Even if the diluent particles possess the same relative shape or size as the catalyst particles, there is still the likelihood that the diluent and catalyst will not be satisfactorily mixed and hot spots can result, as well as the nuisance of having to mix up different catalyst-diluent mixtures for the different reaction zones.

Another solution which has been proposed has been to provide a catalyst, either with or without diluent particles, in which the particle size decreases from inlet to outlet. Such a concept is described in U.S. Pat. No. 3,699,178. However, such a practice, even if the catalyst is utilized without a diluent, requires careful manufacture to assure that the particle sizes are as desired and requires the manufacture of at least two, and very likely three or four different catalysts, in order to attain the objectives of this concept. In the alternative embodiment of this concept, in which the catalyst is intermingled with diluent particles, the disadvantages of utilizing diluent particles are added to those involving the preparation of different sized catalyst particles.

It is an object of the present invention to provide an oxychlorination process for the production of 1,2-dichloroethane from ethylene.

It is a further object of this invention to provide an oxychlorination process for the production of 1,2-dichloroethane from ethylene in which hot spot location and temperature can be readily controlled.

It is another object of the present invention to provide a process for the production of 1,2-dichloroethane by oxychlorination of ethylene at high hydrogen chloride conversion rates.

Another object of the present invention is to provide such a process in which a substantially uniform pressure drop can be maintained for a reasonably long period of time.

Yet another object of the present invention is to provide such a process in which selectivity of conversion of ethylene to 1,2-dichloroethane is acceptably high, and in which excesses of reactants such as ethylene and/or air can be kept to a minimum.

Still another object of the present invention is to provide such a process which can be carried out at high flow rates of reactants.

Another object of the present invention is to provide a system and process for the oxychlorination of ethylene which can be run using either air or oxygen as the oxygen-containing gas.

Yet another object of the present invention is to provide a new catalyst for use in conducting the oxychlorination of ethylene to 1,2-dichloroethane with the above advantages.

SUMMARY OF THE INVENTION

In brief, the invention herein comprises the providing of a novel oxychlorination process utilizing a novel catalyst comprising cupric chloride and potassium chloride supported on a spherically shaped activated alumina having a high surface area and a high structural integrity. Ethylene is converted to 1,2-dichloroethane at high rates of conversion and selectivity with good hot spot control and very little increase in pressure drop over long periods of time by utilizing such a catalyst in a series of three reactors, in which the catalyst is utilized substantially without the presence of an inert diluent, the content and weight ratio of cupric and potassium chlorides in the catalyst being varied within each reactor. In each of the first two reactors, the catalyst bed is divided into two zones, the catalyst in the zone nearest the inlet preferably having a somewhat lower content of cupric chloride and a higher weight ratio of potassium chloride to cupric chloride than the catalyst in the zone nearest the outlet.

In yet another aspect, this invention comprises a system for the carrying out of an oxychlorination process, comprising the aforesaid catalyst situated in reactors as herein described.

More particularly, in one aspect, the invention herein comprises a process for the oxychlorination of ethylene in a fixed bed comprising the steps of:

(a) reacting ethylene, hydrogen chloride and a first portion of an oxygen-containing gas in a first reaction zone in contact with a first catalyst bed substantially undiluted by catalytically inert particles and comprising cupric chloride and potassium chloride supported on spherical particles of activated alumina, the first catalyst bed being divided into two portions in the direction of flow of reactants therethrough, the first portion comprising between about 45% and about 75% of the bed, the second portion comprising between about 25% and about 55% of the bed, the first portion comprising between about 4.5 and about 12.5 weight % cupric chloride and between about 1.5 and about 7 weight % potassium chloride, in a weight ratio of cupric chloride to potassium chloride of between about 1.5:1 and about 4:1, the second portion comprising between about 12 and about 25 weight % cupric chloride and between about 0.5 and about 4 weight % potassium chloride, in a weight ratio of cupric chloride to potassium chloride of between about 5:1 and about 15:1;

(b) reacting the products of step (a) and a second portion of an oxygen-containing gas in a second reaction zone in contact with a second catalyst bed substantially undiluted by catalytically inert particles and comprising cupric chloride and potassium chloride supported on spherical particles of activated alumina, the second catalyst bed being divided into two portions in the direction of flow of reactants therethrough, the first portion comprising between about 45% and about 75% of the bed, the second portion comprising between about 25% and about 55% of the bed, the first portion of the bed comprising between about 5.5 and about 15 weight % cupric chloride and between about 1 and about 5 weight % potassium chloride, in a weight ratio of cupric chloride to potassium chloride of between about 2:1 and about 6:1, the second portion of the bed comprising between about 12 and about 25 weight % cupric chloride and between about 0.5 and about 4 weight % potassium chloride, in a weight ratio of cupric chloride to potassium chloride of between 5:1 and about 15:1; and, (c) reacting the products of step (b) and a third portion of an oxygen-containing gas in a third reaction zone in contact with a third catalyst bed substantially undiluted by catalytically inert particles and comprising between about 12 and about 25 weight % cupric chloride and about 0.5 and about 4 weight % potassium chloride, supported on spherical particles of activated alumina, in a weight ratio of cupric chloride to potassium chloride of between about 5:1 and about 15:1.

In another aspect, this invention comprises a catalyst comprising cupric chloride and potassium chloride supported on a base comprising spherical particles of activated alumina, said base having a BET surface area of between about 225 and about 275 m$^2$/g, an attrition hardness of at least 90%, a total nitrogen pore volume of between about 0.3 and about 0.6 cc/g, an average pore diameter of between about 50 and about 100 Å, between about 20 and about 50% of the pore volume composed of pores having a diameter of between about 80 and 600 Å and further characterized by an X-ray diffraction pattern as hereinafter defined and substantially no observable grain boundaries after etching with HF.

In a third aspect, this invention comprises a reaction system for oxychlorination of ethylene in the presence of a catalyst comprising cupric and potassium chlorides supported on spherical particles of activated alumina, the reaction system comprising:

(a) a first reaction zone comprising a first catalyst bed divided into two portions in the direction of flow of reactants therethrough, the first portion comprising between about 45% and about 75% of the bed, the second portion comprising between about 25% and about 55% of the bed, the first portion comprising between about 4.5 and about 12.5 weight % cupric chloride and between about 1.5 and about 7 weight % potassium chloride in a weight ratio of cupric chloride to potassium chloride of between about 1.5:1 and about 4:1, the second portion comprising between about 12 and about 25 weight % cupric chloride and between about 0.5 and about 4 weight % potassium chloride, in a weight ratio of cupric chloride to potassium chloride of between about 5:1 and about 15:1, (b) a second reaction zone comprising a second catalyst bed divided into two portions in the direction of flow of reactants therethrough, the first portion comprising between about 45% and about 75% of the bed, the second portion comprising between about 25% and about 55% of the bed, the first portion comprising between about 5.5 and about 15 weight % cupric chloride and between about 1 and about 5 weight % potassium chloride, in a weight ratio of cupric chloride to potassium chloride of between about 2:1 and about 6:1, the second portion of the bed comprising between about 12 and about 25 weight % cupric chloride and between about 0.5 and about 4 weight % potassium chloride, in a weight ratio of cupric chloride to potassium chloride of between about 5:1 and about 15:1;

(c) a third reaction zone comprising a third catalyst bed comprising between about 12 and about 25 weight % cupric chloride and between about 0.5 and 4 weight % potassium chloride, in a weight ratio of cupric chloride to potassium chloride of between about 5:1 and about 15:1.

DETAILED DESCRIPTION OF THE INVENTION

The invention will be described with reference to the FIGURE, which depicts an illustrative flow sheet for carrying out the process and utilizing the catalyst and system of the present invention.

The catalyst is prepared by conventional impregnation techniques utilizing aqueous solutions of cupric and potassium chlorides, as further described in the examples which follow. The support which is impregnated is a spherical particulate high surface area activated alumina, that is, an alumina having a BET surface area of at least 100 m$^2$/g, preferably between about 225 and about 275 m$^2$/g, and also an attrition hardness of at least 90%, a total nitrogen pore volume of between about 0.3 and about 0.6 cc/g, and an average pore diameter of between about 50 and about 100 Å, wherein between about 20 and about 50% of the pore volume is composed of pores having a diameter of between about 80 and about 600 Å. The alumina is further characterized by an X-ray diffraction pattern having three main peaks: diffuse peaks at 1.39 and 1.98 Å and another peak at 2.34 Å, the ratio of intensity of the peak at 1.39 Å to that at 1.98 Å being between about 1.5:1 to about 5:1, and by showing substantially no observable grain boundaries after etching with HF. Supports having these properties have been found to have good structural integrity even over lengthy periods of operation. Examples of suitable supports of this type are aluminas currently available under the designations HSC-114, from Houdry Process and Chemical Company and SCM-250, from Rhone-Progil.

Figure 1:
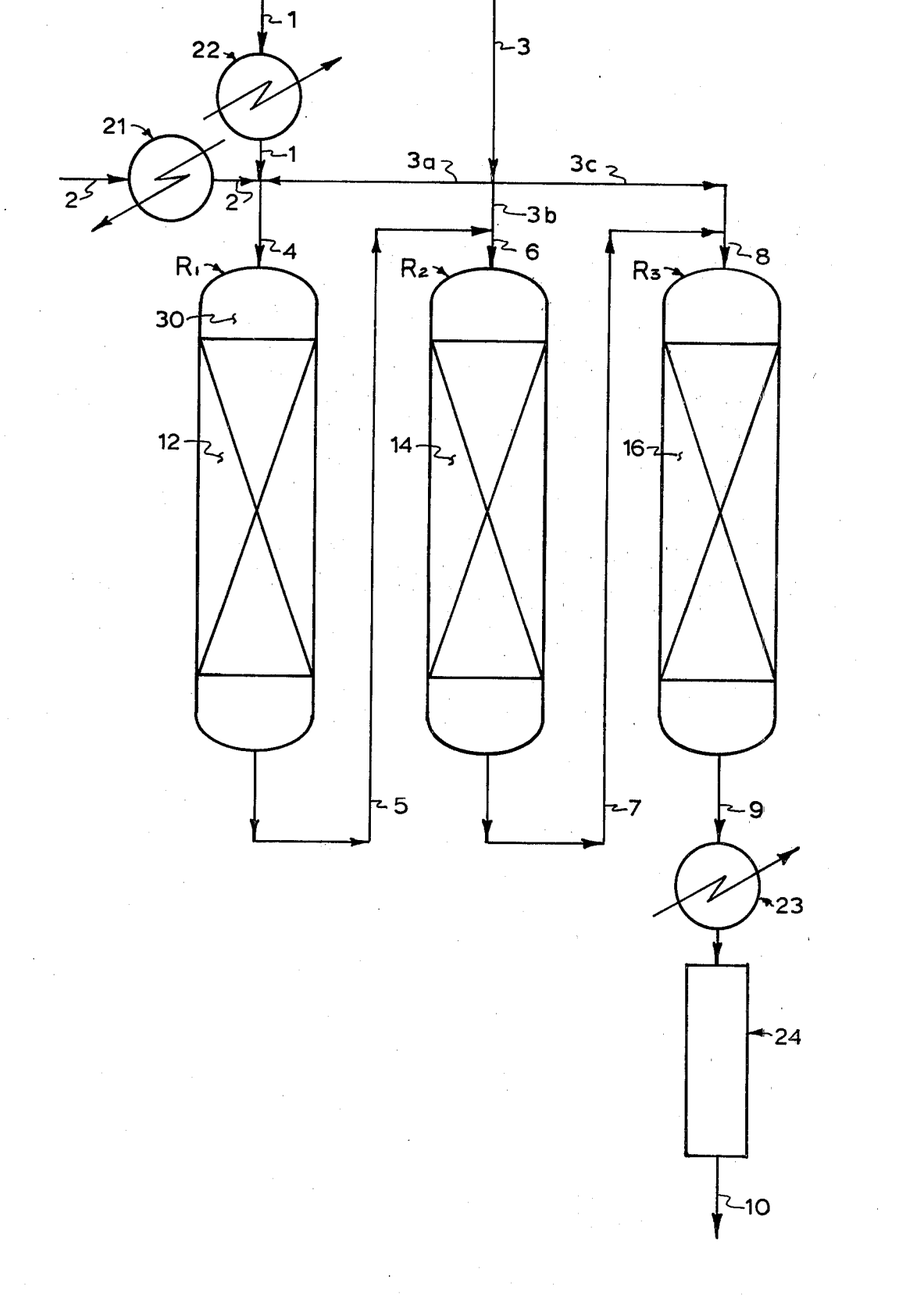

As seen in the FIGURE, the process is conducted in three reactors in series, designated $R_1$, $R_2$ and $R_3$. Each of the reactors contains a catalyst bed, 12, 14, and 16 respectively. The reactors are preferably tubular reactors, having tubes packed with the catalyst. In reactor $R_1$, the catalyst bed is divided into two parts in the direction of the flow of reactants therethrough. The first part, at the inlet side of the reactor, comprises between about 45 and about 75%, preferably between about 55 and about 65%, of the length of the catalyst bed and contains a catalyst having between about 4.5 and about 12.5, preferably between about 5 and about 8, and most preferably between about 5.5 and about 6.5 weight % cupric chloride, and between about 1.5 and about 7, preferably between about 2 and about 4, and most preferably between about 2.7 and 3.3 weight % potassium chloride, wherein the weight ratio of cupric chloride to potassium chloride is between about 1.5:1 and 4:1, preferably between about 1.5:1 and 3:1, and most preferably about 2:1. The second half of the bed, at the outlet end of the reactor, comprises correspondingly between about 25 and about 55%, preferably between about 35 and about 45%, of the bed length and contains a catalyst having between about 12 and about 25 weight %, preferably between about 15 and about 20 weight %, cupric chloride, between about 0.5 and about 4 weight %, preferably between about 1.5 and about 3 weight %, of potassium chloride, the weight ratio of cupric to potassium chlorides being between about 5:1 and about 15:1, preferably between about 5:1 and about 12:1, most preferably about 10:1. Thus, the catalyst bed 12 of reactor $R_1$ contains two types of catalysts: a first catalyst in the section of the bed towards the inlet, having a relatively lower activity in order to ensure that the reaction does not become uncontrollable in its early stages, and a second catalyst having a higher cupric chloride content and therefore, a higher activity, in the portion of the reactor towards the outlet, to continue the reaction at the point at which the reaction begins to lose vigor due to the consumption of oxygen.

Reactor $R_2$ contains catalyst bed 14 which is also divided into two portions. The first portion of the catalyst bed, at the inlet side of the reactor, comprises between about 45 and about 75%, preferably between about 55 and about 65%, of the bed length and the second portion, toward the outlet end, comprises between about 25 and about 55%, preferably between about 35 and about 45%, correspondingly, of the bed length. The catalyst in the first portion of the bed 14 in reactor $R_2$ can be somewhat stronger or more active than the catalyst in the first portion of the bed 12 in reactor $R_1$ since the reaction has already proceeded partway towards completion. In reactor $R_2$, the catalyst in the first portion of the bed contains between about 5.5 and about 15%, preferably between about 7.5 and about 12.5%, and most preferably between about 9 and about 11 weight % cupric chloride, and between about 1 and about 5, preferably between about 1.5 and about 3.5, and most preferably between about 2.5 and about 3.5 weight % potassium chloride, the weight ratio of cupric chloride to potassium chloride being between about 2:1 and about 6:1, preferably between about 3:1 and about 4:1, most preferably about 10:3 (3.3:1). Similarly to reactor $R_1$, the second portion of the catalyst bed of reactor $R_2$ contains a stronger catalyst, which has between about 12 and about 25 weight %, preferably between about 15 and about 20 weight %, cupric chloride and between about 0.5 and about 4 weight %, preferably between about 1.5 and about 3 weight % potassium chloride, the weight ratio of cupric to potassium chloride being between about 5:1 and about 15:1, preferably between about 5:1 and about 12:1, most preferably about 10:1. Similarly to reactor $R_1$, since the reaction has been dropping in intensity as the gases pass through the catalyst bed, due to the consumption of oxygen, the danger of undesirably high localized temperatures in the portion of the bed nearest the outlet is much less than that in the portion near the inlet and therefore a more active catalyst can, and in fact should, be used for best conversions.

In both reactors $R_1$ and $R_2$, the weight ratio of potassium chloride to cupric chloride is preferably higher in the first portion of the catalyst bed than in the second portion.

Entering reactor $R_3$, the reaction has proceeded most of the way toward completion and there is much less danger of undesirably high localized temperatures in comparision to reactors $R_1$ and $R_2$. Therefore, the entire bed of reactor $R_3$ can consist of the more active catalyst utilized in the lower sections of beds 12 and 14, that is a catalyst containing between about 12 and about 25 weight %, preferably between about 15 and about 20 weight % cupric chloride, and between about 0.5 and about 4 weight %, preferably between about 1.5 and about 3 weight %, potassium chloride, with the weight ratio of cupric to potassium chlorides being between about 5:1 and about 15:1, preferably between about 5:1 and about 12:1, most preferably about 10:1. It may also be possible to utilize such a catalyst in reactor $R_3$ and/or the portions of the catalyst beds 12, 16 nearest the outlet in reactors $R_1$ and $R_2$ with an even lower potassium chloride content and higher weight ratio of cupric to potassium chloride.

In the operation of the process of the present invention, hydrogen chloride gas is introduced through line 1 and preheated in preheater 22. Ethylene is introduced in line 2, preheated in preheater 21 and combined with the hydrogen chloride feed in line 1. An oxygen-containing gas, which may be air, molecular oxygen or oxygen-enriched air is introduced through line 3 and divided into three portions in lines 3a, 3b and 3c, respectively. The division may be into three equal or unequal portions. The portion in line 3a is combined with the mixed hydrogen chloride-ethylene feed in line 1 and introduced into reactor $R_1$ through line 4. The temperature of the mixed gaseous feed is generally about 120°-220° C., preferably about 135°-180° C. The mixed feed passes through catalytic bed 12 which, as explained previously, preferably consists of catalyst packed in tubes, and is withdrawn from the reactor in line 5.

The products of reactor $R_1$ in line 5 are combined with the second portion of oxygen-containing gas in line 3b, introduced into reactor $R_2$ via line 6 and contacted with catalyst in bed 14. Reaction products are removed via line 7, contacted with a third portion of oxygen-containing gas in line 3c and introduced via line 8 into catalytic bed 16 of reactor $R_3$. The reaction products are removed in line 9, preferably cooled in heat exchanger 23 and condensed in product condenser 24. The reaction products are recovered in line 10 and consist primarily of 1,2-dichloroethane, with small amounts of ethyl chloride and other chlorinated hydrocarbons.

In general, the process is carried out at an overall system pressure of between about 30 and about 100 psig, preferably between about 40 and about 90 psig. In order to maintain temperature control in reactors $R_1$, $R_2$ and $R_3$, these reactors are preferably constructed as jacketed reactors, the jacket surrounding the tubes or catalyst beds containing a heat exchange fluid such as boiling water, steam or Dowtherm ® fluid. In general, the reaction is conducted at temperatures of between about 180° and about 340° C., preferably between about 235° and about 300° C. In reactor $R_1$, the hot spot temperature is generally maintained below about 330° C., preferably below about 300° C. In reactor $R_2$, the hot spot temperature is maintained generally below 330° C. and preferably also below 300° C. and in reactor $R_3$, the hot spot is maintained at generally below 320° C., preferably below 300° C. Another important factor is the control of the location of the hot spot in the reactors. In each reactor, the hot spot should be located toward the inlet end of the catalyst bed. In reactors $R_1$ and $R_2$, the hot spot should, in fact, be located toward the inlet side in the first, or less active portion of the bed. If the hot spot occurs too far toward the outlet of the bed, it is an indication that the reaction is proceeding too slowly in the bed, that is, that the catalyst is not being used efficiently. Additionally, if the hot spot occurs too far toward the outlet of the bed, it may produce a cumulative result with the reaction-boosting effect of the stronger catalyst in the second portion of the bed, resulting in an undesirably high temperature level at that point.

The division of the oxygen-containing gas among lines 3a, 3b and 3c can be performed such that equal amounts enter all three reactors or, as desired, the amount entering each reactor can be varied as is known in the art. A variance in the amount of this gas introduced into each reactor can affect the temperature and the location of the hot spot in the reactor.

For purposes of illustration, the FIGURE depicts a system in which all three reactors are of the downflow type; that is, reactants are introduced at the top of the reactors and products withdrawn at the bottom. The invention may, however, be practiced in either downflow or upflow reactors, with suitable catalyst holddown devices utilized for upflow reactors. Construction of the reactors as alternately downflow and upflow may reduce piping costs. Thus, reactors $R_1$ and $R_3$ could be upflow reactors and reactor $R_2$ a downflow one. Conversely, reactors $R_1$ and $R_3$ could be downflow and $R_2$ upflow.

The hydrogen chloride feed need not all be introduced into the first reactor; a portion may be split off and introduced into reactor $R_2$, with the second portion of the oxygen-containing gas.

In general, the process is operated with an excess of both oxygen-containing gas and ethylene with respect to hydrogen chloride in order to ensure as complete conversion of hydrogen chloride as possible. When using air, it is desirable to maintain as low an excess of these reactants as possible in order to avoid the handling of large amounts of gas. In such case, the ethylene excess is maintained at a maximum of about 35%, preferably between about 5 and about 20%, and the air excess is maintained at a maximum of about 25%, preferably between about 5 and about 20%.

The invention is described herein primarily in the context of an oxychlorination process in which the oxygen-containing gas is air. However, the catalyst, system and process herein described are also suitable for use in an operation in which molecular oxygen or oxygen-enriched air is employed. In one such process, as described in U.S. Pat. No. 3,892,816, a large excess of ethylene is utilized with respect to the oxygen and hydrogen chloride to prevent overreaction and excessively high hot spots. The excess ethylene is preferably recovered from the reaction product, and recycled to the oxychlorination reactors; thus in such a process, a minimization of ethylene excess is not an objective.

If steel equipment is utilized in the hydrogen chloride flow circuit, small amounts of ferric chloride may be formed and introduced into the catalyst with the feed stream. Corrosion of the oxygen-containing gas supply system can produce iron oxides which can be converted to ferric chloride by reaction with hydrogen chloride in the reactor. The catalyst may contain minor amounts of iron as impurities; however, it has been found that additional ferric chloride, even in small amounts, tends to contaminate and deactivate a cupric chloride oxychlorination catalyst. In one embodiment of the present invention, therefore, ferric chloride contamination of the catalyst is avoided, as shown in the copending application of Ramsey G. Campbell, entitled "Purification of Gas Streams Containing Ferric Chloride", Ser. No. 595,464, filed July 14, 1975 now U.S. Pat. No. 4,000,205, by passing either the hydrogen chloride stream or the mixed gaseous feed stream through a bed of activated alumina impregnated with between about 5 and about 25, preferably between about 10 and about 20 weight % sodium chloride or potassium chloride. The bed may be placed in the hydrogen chloride line 1, either before or after preheater 22, or in the combined feed line 4. Alternatively, it may be located inside $R_1$ at the space 30 adjacent the inlet. In a preferred embodiment, in which tubular reactors are utilized, the bed material may be loaded into the portions of the tubes of reactor $R_1$ adjacent the inlet, ahead of the cupric chloride catalyst in the direction of flow of reactants, and may be separated from it by a screen or the like to prevent migration of removed ferric chloride into the cupric chloride catalyst. In a preferred embodiment, the alumina utilized is the same as that utilized as the catalyst support.

It should be noted that the operation of each of the reactors $R_1$ and $R_2$ is only partially affected by the operation of the other. Thus, for instance, should the location or temperature of the hot spot in either of reactors $R_1$ and $R_2$ be temporarily outside the desired range, the operation of the other reactor would not necessarily be adversely affected or, if it were, it could be possible to separately control operation by adjusting the coolant temperature, division of air between the reactors, etc. Similarly, it is possible, though much less preferred, to utilize the catalyst disclosed herein in the disclosed proportions and bed divisions, in either of reactors $R_1$ or $R_2$ and another suitable, though probably less effective catalyst, in the other. Such an arrangement would not be expected to possess all the advantages of the present invention in terms of throughput, pressure drop, conversion, selectivity, etc., but may be necessary in the event of an emergency or temporary unavailability of catalyst.

To further illustrate the invention in its various embodiments and modifications, the following examples are presented. These in no way are intended to limit the invention, but merely to serve as illustrations thereof.

CATALYST PREPARATION

The catalysts utilized in the following examples were prepared as follows:

A quantity of dry unimpregnated spherically shaped alumina particles was placed in a beaker and weighed. The alumina utlized was HSC-114 alumina obtained from Houdry Process and Chemical Company, and had the following properties:

| | |
|---|---|
| Surface Area, BET | $250 \pm 25$ m$^2$/g |
| Bulk Density | 37–44 lb/cu. ft. |
| Loss of Ignition (300° C.) | 5 wt. %, max. |
| Attrition Hardness | 90%, min. |
| Pore Volume, $N_2$ | 0.44 cc/g |
| Average Pore Diameter, BET | 65–70 Å |
| Pore Volume, 80'600 Å Pores | 20–37% of total pore volume |
| Screen Analysis (Tyler Screen) | |
| +3 mesh | 1.0 max. wt. % |
| −3, +4 mesh | 25–70 wt.% |
| −4, +5 mesh | 25–70 wt.% |
| −5, +6 mesh | 10 max. wt. % |
| −6 mesh | 3 wt.% |

X-ray diffraction data showed three main peaks: at 1.39, 1.98 and 2.34 Å. The peaks at 1.39 and 1.98 Å were diffuse. The X-ray diffraction pattern of gamma-alumina, as given in ASTM file 10-425, has main peaks at the same values. However, ASTM File 10-425 shows the intensities of the peaks at 1.39 and 1.98 Å to be about equal, whereas the diffraction data for the catalysts used in these examples shows the intensity of the peak at 1.39 Å to be about twice that of the 1.98 Å peak.

Results of this type indicate that the support is comprised of (crystalline) gamma-alumina plus an amorphous form of alumina. The amorphous form is possibly rho-alumina, the X-ray diffraction pattern of which has a single broad band at 1.40 Å.

Further investigation of the catalyst's microstructure was performed by HF etching. Samples of new and used catalyst were mounted on a special sample holder and imbedded in an epoxide resin. The samples were cut and polished and chemically etched on a crosssection for 2–5 minutes at room temperature with a 20% HF solution. Observations were made after 20 sec. and 4 minutes at 21X, and after 5 minutes at 85X. No evidence of grain boundaries was observed even after 12 minutes of etching.

Water was added to the beaker in small amounts, the contents being stirred with a glass rod after each addition, until moisture was observed in the beaker. At that point, the alumina was saturated with water. From the final weight of the beaker, the percentage by weight of the absorbed water can be derived. Thus, the amount of water be weight absorbed by the chosen weight of base is determined.

The quantity of dry alumina base to be impregnated was weighed. The quantities of cupric and potassium chlorides which constituted the desired weight percent with reference to the dry base were weighed and dissolved in water. Additional water was added to the resulting solution to bring the volume up to the absorptive capacity of the base as previously determined. It should be noted that it may be necessary to reduce this volume by about 3% to prevent there being a large excess of impregnating solution which is not absorbed by the base. The base and impregnating solution were placed in a drum which was covered, sealed, and rotated for a period of 15 minutes to achieve impregnation.

After 15 minutes, the drum was removed, immediately opened and the saturated alumina particles placed in either glass or ceramic trays to a depth of approximately three inches. The trays were placed in a forced draft oven where the temperature was maintained at 140° C. for 16 to 24 hours. The catalyst was then removed and allowed to cool prior to being stored in air-tight containers.

The weight percents of the salts in the catalyst thus prepared are within 0.5% of the desired values. The accuracy can be enhanced by thorough drying of the alumina base prior to weighing. Drying should immediately follow impregnation; a delay can be detrimental to the physical structure of the resulting catalyst.

The experimental data in the tables which follow was obtained using catalysts prepared according to the foregoing procedure in an apparatus arranged in a flow sequence as in the FIGURE. The three reactors, $R_1$, $R_2$ and $R_3$, each consisted of one schedule 40 nickel pipe, 12.5 feet long and 1 inch in diameter, jacketed for the entire length with a 2½ inch schedule 40 steel pipe, and arranged for downward flow of reactants. The heat of reaction was removed by refluxing Dowtherm ® E in the annular space between the two pipes. The hot spot temperature and location inside the catalytic bed of each reactor was measured by means of a movable thermocouple inside a 12-foot long thermowell which was introduced at the bottom of each reactor.

As shown in the FIGURE, hydrogen chloride was introduced into the system in line 1 through a preheater 22. Ethylene was introduced into the system in line 2 through a preheater 21. Air was introduced into line 3 and split into subconduits 3a, 3b and 3c, the air in line 3a being introduced into reactor $R_1$, that in 3b into reactor $R_2$, and that in 3c into reactor $R_3$. The mixed feed to reactor $R_1$ after preheating was at a temperature of about 140° C. A 100% throughput basis was established as being equivalent to a hydrogen chloride mass velocity in the reactor of 117.6 g.-mole/h-in.$^2$. The air and ethylene feed rates are expressed as a percentage excess based on hydrogen chloride, assuming a stoichiometric reaction to produce 1,2-dichloroethane.

The gas exiting from reactor $R_3$, after pressure reduction, was cooled in a glass water-cooled condenser which condensed all the unreacted hydrogen chloride as an aqueous phase and the majority of the 1,2-dichloroethane produced as a relatively pure (about 98.5%) organic phase. Hydrogen chloride conversion was determined by titrating the aqueous phase with sodium hydroxide to obtain its hydrogen chloride concentration in weight percent.

The uncondensed gas from the water-cooled condenser was analyzed by gas chromatography. The analyses were used to calculate the amount of ethylene oxidation and formation of ethyl chloride, both expressed as a percentage of the ethylene feed.

Table I illustrates conditions of one run of the process according to the present invention, in a preferred embodiment. The run, which continued for a total of 320 hours, was divided into two sections. In the first section, occupying the first 298 hours, the equipment was operated at a 125% throughput of hydrogen chloride and other reactants. During the last 22 hours, the equipment was operated at a 100% throughput rate.

The catalyst to be used was prepared in three formulations. These are shown in Table I as catalysts A, B and C. The desired weight percents of cupric and potassium chlorides were:

Catalyst A 6.0±0.5% $CuCl_2$
3.0±0.3% KCl (weight ratio 2:1)

Catalyst B 10.0±0.7% $CuCl_2$
3.0±0.3% KCl (weight ratio 3.3:1)

Catalyst C 18.0±1.8% $CuCl_2$
1.8±0.25% KCl (weight ratio 10:1)

(Table I shows the amounts found to be present after analysis of the catalysts. The amounts of cupric and potassium chlorides in catalyst C varied somewhat because catalysts from several different preparations were used). In all three reactors, the catalyst bed length was 135 inches; the first (upper) portion, being 81 inches (60% of bed length) and the second (lower) portion being 54 inches in length, or 40% of the total bed length. Catalyst A was utilized in the first portion of the reactor $R_1$ (bed 12); catalyst B was utlized in the first portion of reactor $R_2$ (bed 14): catalyst C was utilized in reactor $R_3$ and the lower portions of reactors $R_1$ and $R_2$.

TABLE I

| Catalyst: | A | B | C |
|---|---|---|---|
| Cupric Chloride-wt.% | 6.1 | 9.9 | 18.4–19.6 |
| Potassium Chloride-wt.% | 3.08 | 3.08 | 1.84–1.92 |
| Iron as Fe-ppm | <800 | <800 | <800 |
| Sulfate as $SO_4$-wt.% | <0.5 | <0.5 | <0.5 |
| Silica as $SiO_2$-wt.% | <0.25 | <0.25 | <0.25 |
| Loss on Ignition at 300° C.-wt.% | <6.0 | <6.0 | <6.0 |
| Hardness-wt% | 93 min. | 94 | 95 |
| Screen Analysis-wt% | | | |
| +3 | 3 max. | 3 max. | 3 max. |
| +4 | 40 min. | 40 min. | 40 min. |
| +5 | 45 max. | 45 max. | 45 max. |
| +6 | 5 max. | 5 max. | 5 max. |
| BET Surface Area-m$^2$/g | 204 | 196.5 | 149–165 |
| Total $N_2$ Pore Volume-cc/g | >0.25 | >0.25 | >0.25 |
| Pore Volume 80–600A | | | |
| Pores-% of total pore volume | >30 | >30 | >30 |
| Average Pore Diameter | | | |
| (BET)-A | >60 | >60 | >60 |

During the first 60 hours of the run, various sources which produced unstable data were corrected and stabilized. Similarly, hours 265 through 298, which occurred between the two portions of the overall run, were occupied by restabilizing the pilot plant following a one-month shut-down between portions of the run.

During operation, as can be seen from the following table, variations were made in the total system pressure, air and ethylene excesses, and division of air between the three reactors, in order to determine the effect of these conditions on hydrogen chloride conversion, selectivity of the reaction to 1,2-dichloroethane, and hot spot temperature and location. The run data and results are given in the following Table II.

TABLE II

| Run Time (hours) | HCl Flow g-mol n-in² | System Pressure (psig) | Air Excess (%) | C₂H₄ Excess (%) | Air Split (R-1/2/3) | HCl Conversion (%) | % of C₂H₄ Oxidized | % of C₂H₄ to EtCl | Hot Spot Temperature and Location (°C./in. from top) R-1 | R-2 | R-3 | Total Pressure Drop (psi) |
|---|---|---|---|---|---|---|---|---|---|---|---|---|
| 0–60 | | | | | Stabilization of plant performance | | | | | | | |
| 60–70 | 147.0 | 70 | 17 | 10 | 33/33/33 | 97.7 | 0.6 | 1.4 | 268/37 | 285/44 | 252/73 | 12.5 |
| 70–83 | 147.0 | 70 | 17 | 13 | 33/33/33 | 98.6 | 0.8 | 1.5 | 285/37 | 288/45 | 253/74 | 13 |
| 83–100 | 147.0 | 70 | 17 | 15.5 | 33/33/33 | 99.3 | 0.9 | 1.4 | 284/37 | 290/45 | 253/56 | 13 |
| 100–120 | 147.0 | 70 | 17 | 10 | 33/33/33 | 98.0 | 0.9 | 1.4 | 286/37 | 290/45 | 255/74 | 12.5 |
| 120–137 | 147.0 | 70 | 17 | 10 | 33/33/33 | 99.5 | 1.9 | 1.5 | 286/37 | 290/45 | 278/36 | 12 |
| 137–144 | 147.0 | 70 | 17 | 10 | 33/33/33 | 98.6 | 1.1 | 1.1 | 287/37 | 292/45 | 258/55 | 12 |
| 144–170 | 147.0 | 80 | 17 | 10 | 33/33/33 | 99.1 | 1.5 | 1.6 | 280/36 | 290/45 | 264/48 | 11 |
| 170–193 | 147.0 | 80 | 10 | 10 | 33/33/33 | 99.0 | 1.4 | 1.6 | 275/37 | 293/45 | 288/37 | 10.5 |
| 193–205 | 147.0 | 80 | 22 | 10 | 33/33/33 | 98.5 | 1.2 | 1.6 | 282/37 | 290/45 | 253/73 | 11.5 |
| 205–230 | 147.0 | 80 | 17 | 10 | 33/33/33 | 99.2 | 1.5 | 1.6 | 278/37 | 293/44 | 268/38 | 11 |
| 230–245 | 147.0 | 80 | 17 | 10 | 38/3328 | 98.9 | 1.1 | 1.4 | 297/45 | 270/48 | 254/57 | 11 |
| 245–265 | 147.0 | 80 | 17 | 10 | 38/28/33 | 98.7 | 1.4 | 1.5 | 300/52 | 286/46 | 262/56 | 11.5 |
| 264–298 | | | One-month shutdown followed by re-stabilizing of plant performance. | | | | | | | | | |
| 293–300 | 117.6 | 63 | 17 | 8 | 33/33/33 | — | — | — | 269/37 | 284/28 | 255/58 | — |
| 300–315 | 117.6 | 66 | 17 | 8 | 33/33/33 | 99.2 | 1.5 | 1.4 | 280/38 | 290/28 | 256/58 | 7.5 |
| 315–320 | 117.6 | 68 | 17 | 8 | 33/33/33 | 99.2 | 1.8 | 1.4 | 294/35 | 295/28 | 260/56 | 7 |
| 320 | 117.6 | 70 | 17 | 8 | 33/33/33 | | | | 297/36 | 301/28 | | 7.5 |

Coolant temperatures maintained as follows: $R_1$ - 210°–215° C., $R_2$ - 209°–215° C., $R_3$ - 219°–227° C.

Similarly to run number 1 described hereinabove, additional runs designated in Table III below as runs 2 through 9, were conducted utilizing various combinations of catalyst compositions and reaction conditions within the scope of this invention. In all cases, as was the case in run number 1, the catalyst bed was 135 inches long. In both $R_1$ and $R_2$, the first zone, at the upper, or inlet, end of the reactor occupied 81 inches, or 60% of the bed, while the second zone occupied 54 inches, or 40% of the total bed length. The catalyst in reactor $R_3$ was similar to that in run number 1. Coolant temperatures were maintained similarly to run number 1.

Thus, a pressure reduction was not required to maintain the hot spot control and the pressure drop did not increase over extended run times due to deterioration of the catalyst. Furthermore, even when operating at high throughput, the ethylene excess could be kept within reasonable limits without substantially affecting hydrogen chloride conversion. As seen from the data in Tables II and III, it was quite possible to operate at ethylene excesses of about 10% while still obtaining as high as 99+% hydrogen chloride conversion.

Additionally, the catalyst in the staging pattern, herein described, has also been found suitable for operation at less than design throughput. Thus the catalyst

TABLE III

| Run # | 2 | 3 | 4 | 5 | 6 | 7 | 8 | 9 |
|---|---|---|---|---|---|---|---|---|
| Duration, h. | 64 | 43 | 54 | 69 | 55.5 | 111.5 | 185 | 16.5 |
| Air Excess, % | 17 | 17 | 17 | 17 | 17 | 17 | 17 | 17 |
| C₂H₄ Excess, % | 10–12 | 8–12 | 8–10 | 10 | 10–3 | 8 | 7 | 8 |
| HCl thoroughput, % | 125 | 125 | 125 | 125 | 125 | 125 | 125 | 125 |
| Catalyst comp.: wt.% CuCl₂: wt.% KCl: | | | | | | | | |
| $R_1$, 1st zone | 6:2 | 5:2 | 6:2 | 6:3 | 10:4 | 12:6.7 | 12:6.7 | 8:3 |
| $R_1$, 2nd zone | 18:1.8 | 18:1.8 | 18:1.8 | 18:1.8 | 18:1.8 | 18:1.8 | 18:1.8 | 18:1.8 |
| $R_2$, 1st zone | 12:2 | 8:2 | 8:2 | 8:2 | 12:3 | 12:3 | 10:3 | 10:3 |
| $R_2$, 2nd zone | 18:1.8 | 18:1.8 | 18:1.8 | 18:1.8 | 18:1.8 | 18:1.8 | 18:1.8 | 18:1.8 |
| HCl Conversion, % | 98.8–99.4 | 98.0–99.1 | 98.4–99.1 | 99.0 | 99.7–99.0 | 99.4–98.2 | 98.5–99.4 | 99.3–98.3 |
| C₂H₄ Oxidized, % | 2.3–2.7 | 1.7 | 2.3 | 2.2 | 1.4–1.9 | 1.3 | 1.3–2.4 | ~1.5 |
| C₂H₄ to C₂H₅Cl, % | 1.4 | 1.5–2.1 | 1.6 | 1.3–1.8 | 1.25 | 1.2 | ~1.2 | ~1.5 |
| Hot Spot Temp. & Location° C./in. from top, averages | | | | | | | | |
| $R_1$ | 310/45 292/60 | 294–334/50 | 365–334/ 40–50 | 260–315/ 95,65 (rising) | 340–275/50 300/58 | 300–325/ 55–60 | 255–340/ 30–100 | 315–345/ 20–35 |
| $R_2$ | 325/35 302/30 | 272/105 305/55 | 315–335/ 42 | 325–340/ 100 | 285/45–60 272/55 | 275–285/ 35–40 | 255–325/ 20–45 | 260–280/ 45 |
| $R_3$ | 260/18–20 313/35 | 245–250/ 50 | 255–265/ 25 | 263/57 | 260–270/ 40–70 | 250+/ 50–75 | 245–270/ 45–75 | 270/75 |
| Pressure Drop, psi | 12.5 | 11 | 11–12 | 13 | 12 | 12.5 | 12.5 | 11 |

In all the runs 1 through 9 above, it can be seen that the use of the catalyst described herein, in the staging patterns described, resulted in maintenance of hot spot temperatures generally below about 340° C. at throughputs as high as 125% of the design throughput. The hot spots were in controllable locations and, in fact, as can be seen, on many occasions they fell far below 300° C. Of equal importance, the pressure drop remained substantially constant throughout the reaction system, even in run 1, in which the run length totaled over 300 hours.

and system herein described possesses versatility and can be utilized in a plant operation in which the throughput can be variable, depending on conditions such as feedstock supply and market demand, over a range from substantially less than design capacity to substantially greater than design capacity, without requiring replacement or modification.

What is claimed is:

1. A reaction system for fixed bed oxychlorination of ethylene with hydrogen chloride and an oxygen-containing gas in the presence of a catalyst comprising cupric and potassium chlorides supported on spherical particles of activated alumina, substantially undiluted by catalytically inert particles, comprising:
   (a) a first reaction zone comprising a first catalyst bed divided into two portions in the direction of flow of reactants therethrough, the first portion comprising between about 45% and about 75% of the bed, the second portion comprising between about 25% and about 55% of the bed, the first portion comprising between about 4.5 and about 12.5 weight % cupric chloride and between about 1.5 and about 7 weight % potassium chloride, in a weight ratio of cupric chloride to potassium chloride of between about 1.5:1 and about 4:1, the second portion comprising between about 12 and about 25 weight % cupric chloride and between about 0.5 and about 4 weight % potassium chloride, in a weight ratio of cupric chloride to potassium chloride of between about 5:1 and about 15:1.
   (b) a second reaction zone comprising a second catalyst bed divided into two portions in the direction of flow of reactants therethrough; the first portion comprising between about 45% and about 75% of the bed, the second portion comprising between about 25% and about 55% of the bed, the first portion comprising between about 5.5 and about 15 weight % cupric chloride and between about 1 and about 5 weight % potassium chloride, in a weight ratio of cupric chloride to potassium chloride of between about 2:1 and about 6:1, the second portion of the bed comprising between about 12 and about 25 weight % cupric chloride and between about 0.5 and about 4 weight % potassium chloride, in a weight ratio of cupric chloride to potassium chloride of between about 5:1 and about 15:1;
   (c) a third reaction zone comprising a third catalyst bed comprising between about 12 and about 25 weight % cupric chloride and between about 0.5 and about 4 weight % potassium chloride in a weight ratio of cupric chloride to potassium chloride of between about 5:1 and about 15:1;
   (d) means for introducing the ethylene into the first reaction zone;
   (e) means for introducing the hydrogen chloride into the first reaction zone; and
   (f) means for introducing the oxygen-containing gas into each of the first, second and third reaction zones.

2. A reaction system according to claim 1 in which the first portion of the first catalyst bed comprises between about 55 and about 65% of the bed, and the second portion of the first catalyst bed comprises between about 35% and about 45% of the bed.

3. A reaction system according to claim 1 in which the first portion of the first catalyst bed comprises between about 5 and about 8 weight % cupric chloride and between about 2 and about 4 weight % potassium chloride in a weight ratio of cupric chloride to potassium chloride of between about 1.5:1 and about 3:1.

4. A reaction system according to claim 1 in which the first portion of the first catalyst bed comprises between about 5.5 and about 6.5 weight % cupric chloride and between about 2.7 and about 3.3 weight % potassium chloride.

5. A reaction system according to claim 1 in which the weight ratio of cupric chloride to potassium chloride in the first portion of the first catalyst bed is about 2:1.

6. A reaction system according to claim 1 in which the first portion of the second catalyst bed comprises between about 55 and about 65% of the bed.

7. A reaction system according to claim 1 in which the first portion of the second catalyst bed comprises between about 7.5 and about 12.5 weight % cupric chloride and between about 1.5 and about 3.5 weight % potassium chloride, in a weight ratio of cupric chloride to potassium chloride of between about 3:1 and about 4:1.

8. A reaction system according to claim 1 in which the first portion of the second catalyst bed comprises between about 9 and about 11 weight % cupric chloride and between about 2.5 and about 3.5 weight % potassium chloride.

9. A reaction system according to claim 1 in which the weight ratio of cupric chloride to potassium chloride in the first portion of the second catalyst bed is about 10:3.

10. A reaction system according to claim 1 in which the second portion of the first catalyst bed comprises between about 12 and about 25 weight % cupric chloride and between about 0.8 and about 4 weight % potassium chloride, in a weight ratio of cupric chloride to potassium chloride of between about 5:1 and about 15:1.

11. A reaction system according to claim 1 in which the second portion of the second catalyst bed comprises between about 12 and about 25 weight % cupric chloride and between about 0.8 and about 4 weight % potassium chloride, in a weight ratio of cupric chloride to potassium chloride of between about 5:1 and about 15:1.

12. A reaction system according to claim 1 in which the third catalyst bed comprises between about 12 and about 25 weight % cupric chloride and between about 0.8 and about 4 weight % potassium chloride in a weight ratio of cupric chloride to potassium chloride of between about 5:1 and about 15:1.

13. A reaction system according to claim 1 in which the second portion of the first catalyst bed comprises between about 15 and about 20 weight % cupric chloride and between about 1.5 and about 3 weight % potassium chloride, in a weight ratio of cupric chloride to potassium chloride of between about 5:1 and about 12:1.

14. A reaction system according to claim 1 wherein the weight ratio of cupric chloride to potassium chloride in the second portion of the first catalyst bed is about 10:1.

15. A reaction system according to claim 1 in which the second portion of the second catalyst bed comprises between about 15 and about 20 weight % cupric chloride and between about 1.5 and about 3 weight % potassium chloride in a weight ratio of cupric chloride to potassium chloride of between about 5:1 and about 12:1.

16. A reaction system according to claim 15 in which the weight ratio of cupric chloride to potassium chloride in the second portion of the second catalyst bed is about 10:1.

17. A reaction system according to claim 1 in which the third catalyst bed comprises between about 15 and about 20 weight % cupric chloride and between about 1.5 and about 3 weight % potassium chloride in a weight ratio of cupric chloride to potassium chloride of between about 5:1 and about 12:1.

18. A reaction system according to claim 17 in which the weight ratio of cupric chloride to potassium chloride in the third catalyst bed is about 10:1.

19. A reaction system according to claim 1 in which the reaction zones comprise tubular reactors, the respective catalysts being contained in the tubes thereof.

20. A reaction system according to claim 19 further comprising spherical particles of alumina impregnated with a member selected from the group consisting of sodium chloride and potassium chloride, situated in the tubes of the first reaction zone adjacent to the inlet side thereof, ahead of the catalyst bed in the direction of flow of reactants.

21. A reaction system according to claim 20 in which the member is potassium chloride.

* * * * *